US006616876B1

(12) United States Patent
Labrecque et al.

(10) Patent No.: US 6,616,876 B1
(45) Date of Patent: Sep. 9, 2003

(54) METHOD FOR TREATING EXPANDABLE POLYMER MATERIALS

(75) Inventors: Roger Labrecque, Dracut, MA (US); Joseph Ferraro, Londonderry, NH (US); Tom Swanick, Nashua, NH (US); Paul Martakos, Pelham, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/678,765

(22) Filed: Oct. 3, 2000

(51) Int. Cl.$^7$ .................. B29B 11/10; B29B 13/00; B29C 47/00; B29C 55/00
(52) U.S. Cl. .................. 264/119; 264/109; 264/126; 264/127; 264/134; 264/291; 264/343
(58) Field of Search .................. 264/109, 119, 264/125, 126, 127, 291, 343, 134

(56) References Cited

U.S. PATENT DOCUMENTS

| | | | | |
|---|---|---|---|---|
| 3,847,676 A | * | 11/1974 | Palmer et al. | 264/211 |
| 3,862,030 A | | 1/1975 | Goldberg | 210/24 |
| 3,918,995 A | * | 11/1975 | Palmer et al. | 264/176 |
| 4,177,334 A | | 12/1979 | Okita | 521/145 |
| 4,187,390 A | | 2/1980 | Gore | 174/102 |
| 4,598,011 A | | 7/1986 | Bowman | 428/221 |
| 4,938,911 A | | 7/1990 | Bastiaansen et al. | 264/56 |
| 5,064,593 A | | 11/1991 | Tamaru et al. | 264/113 |
| 5,411,550 A | | 5/1995 | Herweck et al. | 623/1 |
| 5,429,869 A | * | 7/1995 | McGregor et al. | 428/364 |
| 5,476,589 A | | 12/1995 | Bacino | 210/500 |
| 5,552,100 A | | 9/1996 | Shannon et al. | 264/127 |
| 5,641,373 A | | 6/1997 | Shannon et al. | 156/242 |
| 5,721,283 A | | 2/1998 | Howard, Jr. et al. | 521/60 |
| 5,788,626 A | | 8/1998 | Thompson | 600/36 |
| 5,800,522 A | | 9/1998 | Campbell et al. | 623/1 |
| 5,824,050 A | | 10/1998 | Karwoski et al. | 623/1 |
| 5,843,173 A | | 12/1998 | Shannon et al. | 623/1 |
| 5,897,587 A | | 4/1999 | Martakos et al. | 623/1 |
| 6,030,428 A | | 2/2000 | Ishino et al. | 55/486 |
| 6,120,939 A | * | 9/2000 | Whear et al. | 429/254 |

FOREIGN PATENT DOCUMENTS

| | | |
|---|---|---|
| EP | 106496 A2 | 4/1984 |
| EP | 288021 A2 | 10/1988 |
| EP | 288021 A3 | 10/1988 |
| WO | WO 98/26731 A2 | 6/1998 |
| WO | WO 98/26731 A3 | 6/1998 |

OTHER PUBLICATIONS

Patent Abstracts of Japan, vol. 003, No. 109 (C–058), Sep. 12, 1979, JP 54086573 A (Nitto Electric Ind. Co. Ltd. (Jul. 10, 1979), abstract.
Patent Abstracts of Japan, vol. 018, No. 317 (M–1622), Jun. 16, 1994, JP 06071744 A (Dai ichi Kogyo Seiyaku Co., Ltd.; Others: 01) (Mar. 15, 1994), abstract.

* cited by examiner

Primary Examiner—Stephen J. Lechert, Jr.
(74) Attorney, Agent, or Firm—Lahive & Cockfield, LLP

(57) ABSTRACT

The invention is directed to methods involving rewetting of expandable polymers with a wettable liquid to allow for enhanced expansion at or below room temperature without breakage, and in some cases, allows one to achieve a greater expansion ratio than that allowed at elevated temperatures using known methods. The present invention also allows one to achieve material with unique properties and handling characteristics. These properties included decreased material thickness, increased density, an altered node/fibril morphology, and a more consistent web in the case of flat material. This method is not limited to room temperature conditions and can be applied whenever the expandable polymer material is wet with a wettable liquid, and the expansion is performed at a temperature preferably below the vaporization or boiling points of that liquid.

36 Claims, 17 Drawing Sheets

METHOD FOR TREATING EXPANDABLE POLYMER MATERIALS

TECHNICAL FIELD

The present invention relates generally to materials and processing of materials. More specifically, the present invention is directed to expandable polymers and methods for processing of expandable polymers.

BACKGROUND

A conventional method of forming an article made of an expandable polymer, such as PTFE, is to blend a powdered resin with a wettable liquid, such as a lubricant or extrusion aid, and compress the combination under relatively low pressure into a preformed billet. A wettable liquid is mixed with the powdered resin to control the degree of material shear that occurs during subsequent extrusion and to prevent excessive shear, which can damage the material.

Using a ram-type extruder, the billet is extruded through a die having a desired cross-section. Next, the wettable liquid is removed from the extruded material by drying or by another extraction method. The dried extruded material is then stretched in one or more directions at an elevated temperature below the crystalline melting point of the resin. In the case of PTFE, this results in the material taking on a microstructure characterized by elongated nodes interconnected by fibrils. Typically, the nodes are oriented with their elongated axis perpendicular to the direction of stretching.

According to conventional methods, there is a direct relationship between temperature and maximum expansion ratio while maintaining material uniformity and without breakage of the material. At low expansion temperatures, the material shows inconsistencies, is weak, and often breaks. Typically, heating well above room temperature is required to prevent the expandable polymer material from breaking and to ensure uniform material thickness after expansion.

U.S. Pat. No. 4,187,390 describes a method of forming porous PTFE that requires stretching at elevated temperatures. Material expanded at lower temperatures often fractures or results in weak material.

U.S. Pat. No. 5,552,100 describes a method of forming thin porous fluoropolymer films by post-sinter stretching the material to a final thickness less than 0.002 inches. The conventional manufacturing of films having thicknesses below 0.002 inches during pre-sinter expansion often result in breaking or tearing of the film.

Therefore, a need exists for a method providing substantial expansion of expandable polymers, without need for heating, to create uniform material with alternate polymer morphologies. Furthermore, the ability to decrease thickness, increase strength, uniformity and density of expandable polymers is desirable in many applications.

SUMMARY

The present invention is directed generally to methods for treating expandable polymers and products produced therefrom. More particularly, the invention relates to methods for forming an article from an expandable polymer that has been stretched involving the steps of rewetting the expandable polymer with a wettable liquid to form a wetted material, and stretching the wetted material. Preferably, the wettable liquid is later removed.

According to another aspect of the invention, an article is formed by rewetting an expandable polymer and then stretching the expandable polymer.

Expandable polymer articles formed in accordance with the processes of the invention have characteristics, such as uniformity, porosity, density, node size, thickness, fibril density and permeability not attainable from conventional methods.

These and other features, aspects, and advantages of the present invention will become better understood with reference to the following description and appended claims.

BRIEF DESCRIPTION OF THE DRAWINGS

The subject matter regarded as the invention is particularly pointed out and distinctly claimed in the concluding portion of the specification. The invention, however, both as to organization and method of practice, together with further objects and advantages thereof, is best understood by reference to the following illustrative descriptions taken in conjunction with the accompanying drawings in which like numerals refer to like elements.

DETAILED DESCRIPTION

Figure 1A:
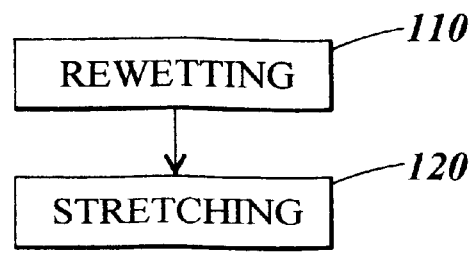
FIG. 1A illustrates an exemplary method of a first embodiment of the invention.

The present invention provides a means to expand expandable polymers at or below room temperature without breakage and maintaining a substantially uniform material, and allows one to achieve a greater expansion ratio than that allowed at elevated temperatures using known methods.

Polymers with ordered microstructures often referred to as highly crystalline, have the fundamental ability to expand into another shape and size. Fluoropolymers and polyolefins are polymers suitable for expansion processes. Fluoropolymers include homopolymers of polytetrafluoroethylene (PTFE), and copolymers of polytetrafluoroethylene in which the comonomer is ethylene, chlorotrifluoroethylene, perfluoroalkoxytetrafluoroethylene, and fluorinated propylene. Polyolefins include polypropylene and polyethylene.

The concept of contact angle and its' equilibrium is valuable because it can be used to define wettability. When a liquid wets a solid, it spreads freely over the surface at a rate depending on the liquid viscosity and surface tension, and solid surface roughness, porosity, and chemistry. The tendency for the liquid to spread increases as contact angle decreases so contact angle is a useful inverse measure of wettability. Contact angle is the angle measured which the liquid makes with a solid. The contact angle of a liquid is a result of the thermodynamic equilibrium of a drop on a solid surface. Solids, liquids, and gases, exist in equilibrium. At the interface between a liquid and solid, the interfacial monolayer of the liquid is attracted by the bulk liquid and gas from one side and from the other side by the intermolecular forces which interact between the solid and liquid. A porous material is said to be "wet" when the voids of the material are at least partially occupied by a given fluid.

In accordance with the invention, multi-directional expansion of an expandable polymer (sintered or unsintered) can occur at room temperature provided the material is rewet with a wettable liquid before or during the expansion step. Rewetting involves the application of wettable liquid after completion of activities for which wettable liquid may be used, such as extrusion. Removal of any previous wettable liquid is not required before rewetting. This method is not limited to room temperature conditions and can be applied whenever the expandable polymer is rewet with the wettable liquid. Ideally, the expansion is performed at a temperature below the vaporization or boiling points of the wettable liquid.

Wet stretch is defined herein as the expansion or deformation of an expandable polymer in one or more directions when the material is wet with a wettable liquid before or during the expansion step. Wet stretching of an expandable polymer resin, such as PTFE, can provide: modified processability, material structures which differ from those made from conventionally processed resin, for example, decreased thickness, increased density, and product uniformity. The overall feel of the product is typically enhanced, due to increased smoothness.

Major differences can be seen in the structures according to the invention compared to conventionally processed material. The invention typically provides increased density and improved strength, allowing products to be thinner than those made from conventional methods.

The extrudate may also be sintered, after stretching or before stretching, by heating it to a temperature above its crystalline melting point wile being maintained in a stretched condition. This can be considered an amorphous locking process for permanently "locking-in" the microstructure in the expanded or stretched configuration. The methods of the invention can simultaneously provide greatly reduced sintering times and improved product structure over conventional methods. The present invention does not require sintering for certain applications, including endovascular, filtration, and the like, as is typically required by conventional methods.

The ability to increase the amount of expansion in either sintered or unsintered expandable polymers has a wide variety of applications in medical, industrial, and consumer products. For example: laminate structures with varying properties for filters and membranes; medical implants with tailored porosities to control body fluid leakage and tissue ingrowth; radially expandable PTFE with reduced expansion force and/or increased expansion ratios for endovascular applications.

A variety of forms and sizes are included in the scope of the invention. For example, flat sheets, hollow tubes, and solid rods, can be manufactured and utilized in many applications. Furthermore, the invention is applicable to any structures formable by conventional expandable polymer methods.

Expanded PTFE material is characterized by lengthwise-oriented fibrils interrupted by transverse nodes. The pore size in microns is typically determined by measuring fiber length between-the nodes (intemodal distance). To compute fibril length, the material is viewed under sufficient magnification. A fibril length is measured from one edge of one node to the edge of an adjacent node. Fibril lengths are measured from the sample to compute a mean fibril length.

Nodes and fibrils may be further characterized by their relative geometry. That is, nodes by length, width, and height; and fibrils, by diameter and length. It is the relative geometry of nodes to fibrils, as well as, internodal distance and fibril density that determines porosity and permeability of porous PTFE. The physical space between connecting nodes is composed of solid thread like PTFE fibers called fibrils in conjunction with a gaseous void volume. Fibril density refers to the relative volume consumed by fibrils between the nodes.

Permeability or hydraulic conductivity is related to material porosity. Permeability to fluid flow can be determined by measuring the amount of pressure required for water to permeate the pores of the material. Water entry pressure (WEP) is a good measuring technique to assess this trait because it closely mimics the permeation process at the liquid/solid interface. WEP is defined as the pressure value necessary to push water into the pores of a synthetic tubular substrate and can be classified as: High(>400 mm Hg), Medium (200–400 mm Hg), and Low (<200 mm Hg). To compute WEP, the material is subjected to an incrementally increasing water pressure until small beads of water appear on the surface.

Machine direction (MD) refers to the direction in which the polymeric material travels through the processing machine. Transverse direction (TD) refers to the direction that is perpendicular to the MD. Longitudinal Tensile Strength (LTS) is measured in pounds per square inch by dividing the tensile force applied to the material by the cross-sectional area of the material. Radial Tensile Strength (RTS) is also measured in pounds per square inch. RTS is obtained by dividing the radial expansion force applied to the material by the cross-sectional area of the material.

Cross-sectional area is the amount of material subjected to a controlled strain during tensile testing defined as the sample width multiplied by its thickness.

Suture Retention strength (SRT), measured in pounds, indicates the amount of force needed to pull out sutures from the polymeric material.

The invention will now be described with reference to two exemplary embodiments. Cylinders, tubes, sheets, or other shapes can be created by either of these embodiments.

Both embodiments involve the use of expandable polymers. Although expandable polymer material may be prepared in a variety of ways, one method involves the use of wettable liquid to aid an initial extrusion process. A wettable liquid is capable of entering the pores of the expandable polymer resin. The invention is not limited to expandable polymers prepared by extrusion, or by the use of a wettable liquid for extrusion.

By way of example, an expandable polymer resin, such as PTFE resin (Fluon CD-123 obtained from ICI Americas), may be blended with a first wettable liquid, such as ISOPAR-H odorless solvent (produced by EXXON Corporation), to form a lubricated powder. The wettable liquid may be mixed with the resin to control the degree of material shear that occurs during subsequent extrusion and to prevent excessive shear, which can damage the material. By application of pressure, the lubricated powder may then be preformed into a billet, typically shaped like a large cylinder.

Using a ram-type extruder, the billet may be extruded through a die having a desired cross-section, typically a circle, thereby forming a cylinder. A variety of shapes may be formed by extrusion, such as a solid or hollow cylinder, a flat sheet, a rectangle and the like.

Figure 1B:
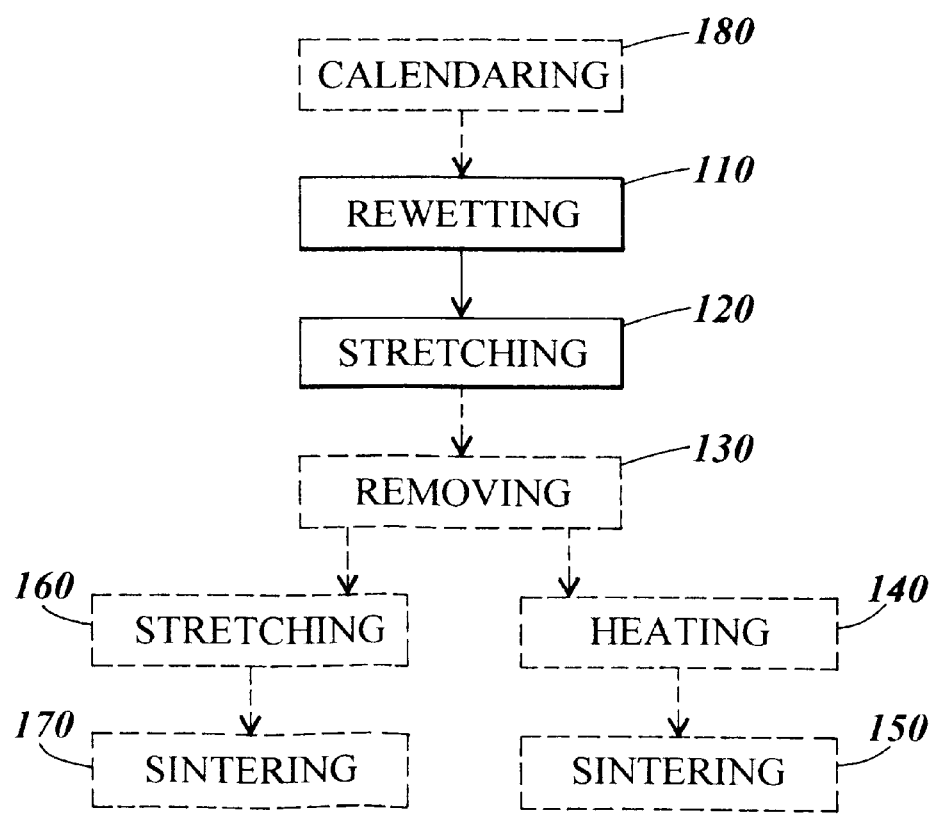
FIG. 1B illustrates exemplary variations of a first embodiment of the invention.

The first embodiment of the invention is described with reference to FIG. 1. An expandable polymer is rewet, step 110, with a second wettable liquid such as ISOPAR-H. Rewetting may be performed by exposing the expandable polymer to the second wettable liquid, such as by submerging or soaking the expandable polymer in the second wettable liquid, spraying the second wettable liquid, or rubbing the second wettable liquid into the expandable polymer. As described above, rewetting involves the application of wettable liquid after completion of activities for which wettable liquid may be used, such as extrusion. Removal of any previous wettable liquid is not required before rewetting.

Use of the second wettable liquid results in substantially uniform material with increased density and substantially altered node structure. Ideally, the second wettable liquid completely saturates the expandable polymer. As with all embodiments described herein, elevated temperature or pressure above ambient conditions may be used in conjunction with the application of a wettable liquid to reduce the time necessary for saturation or aid in saturation of the expandable polymer.

Stretching, step 120, is then performed, preferably at a temperature below a boiling point of the second wettable liquid. Stretching can be performed in more than one direction. Stretching is typically performed, in the case of a cylinder, by applying tensile force to the ends of the cylinder. In the case of a flat sheet, stretching is typically performed in the machine direction. Alternatively, or in addition, stretching may be performed in the radial or transverse direction to a cylinder or flat sheet, respectively. For example, in the case of a hollow cylinder, a mandrel may be used to radially stretch the hollow polymer cylinder. Tensile force may be applied to stretch the cylinder simultaneously with the use of a mandrel or at a different time. Within the scope of the invention, a combination of various stretching may be combined or applied in succession.

As with all embodiments described herein, heat may also be applied to the expandable polymer prior to or during stretching. It is preferable to keep the temperature of the expandable polymer below a boiling point of the second wettable liquid to inhibit loss of the second wettable liquid.

Although ISOPAR-H is used as the first and second wettable liquids in this embodiment, other permeating liquids are within the scope of the invention and can be considered interchangeable with ISOPAR-H or other wettable liquids. As an example, polyethylene glycol is preferred for in vivo applications because it is a biocompatible liquid. Naphtha is another example of a wettable liquid that may be used within the scope of the invention. Alcohol and water may also be used in combination. It is also within the scope of the invention to use one wettable liquid during the initial extrusion process and another wettable liquid for rewetting. Also, a combination of liquids may be used during either extrusion or rewetting.

Optionally, further steps of the preferred embodiment of the invention may include removing the second wettable liquid, step 130. Although removal can be accomplished at room temperature, heating to an elevated temperature is preferred to accelerate removal of the second wettable liquid. Optional heating, step 140, to for example, 320° C., can be performed following removal of the second wettable liquid, step 130. Heating, step 140, may optionally be sufficient to cause sintering, typically at about 360° C., thereby locking in the microstructure. Alternatively, sintering, step 150, may be conducted after heating.

A further alternative of the first embodiment involves a second stretching step 160, after optional removing of the wettable liquid, step 130. As discussed above, this second stretching step 160 may involve heating prior to or during stretching and may be conducted in the machine direction, a transverse direction, or any combination or sequential application thereof. Sintering, step 170, may optionally be performed after the second stretching.

A further variation of the first embodiment of the invention includes calendaring, step 180, before the rewetting step 110. Calendaring is preferably performed during the creation of flat sheets after extrusion of the expandable polymer. Preferably, calendaring rolls are operated at an elevated temperature, such as, for example, 130° F.

Figure 2A:
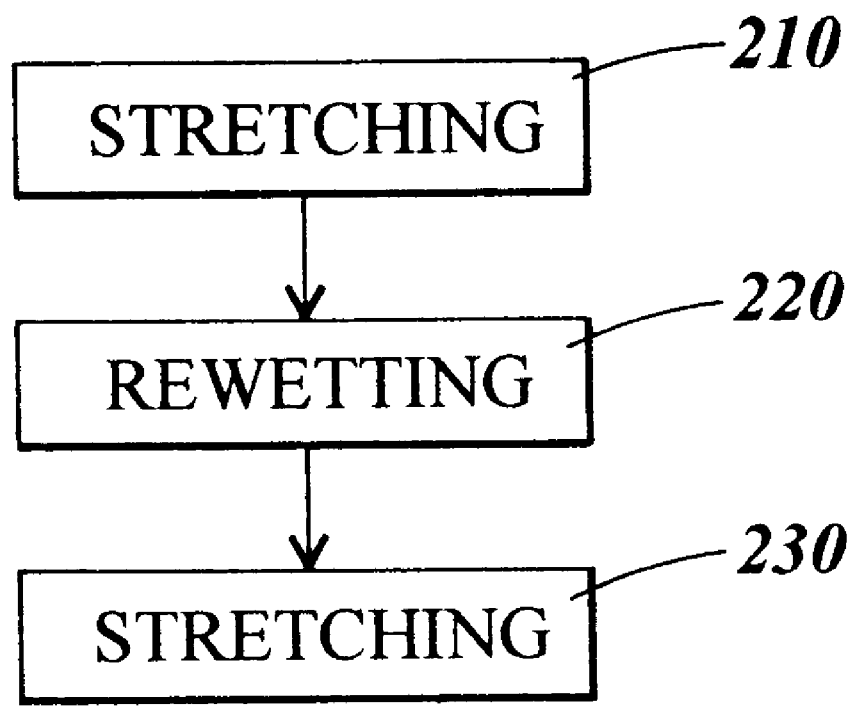
FIG. 2A illustrates an exemplary method of a second embodiment of the invention.
Figure 2B:
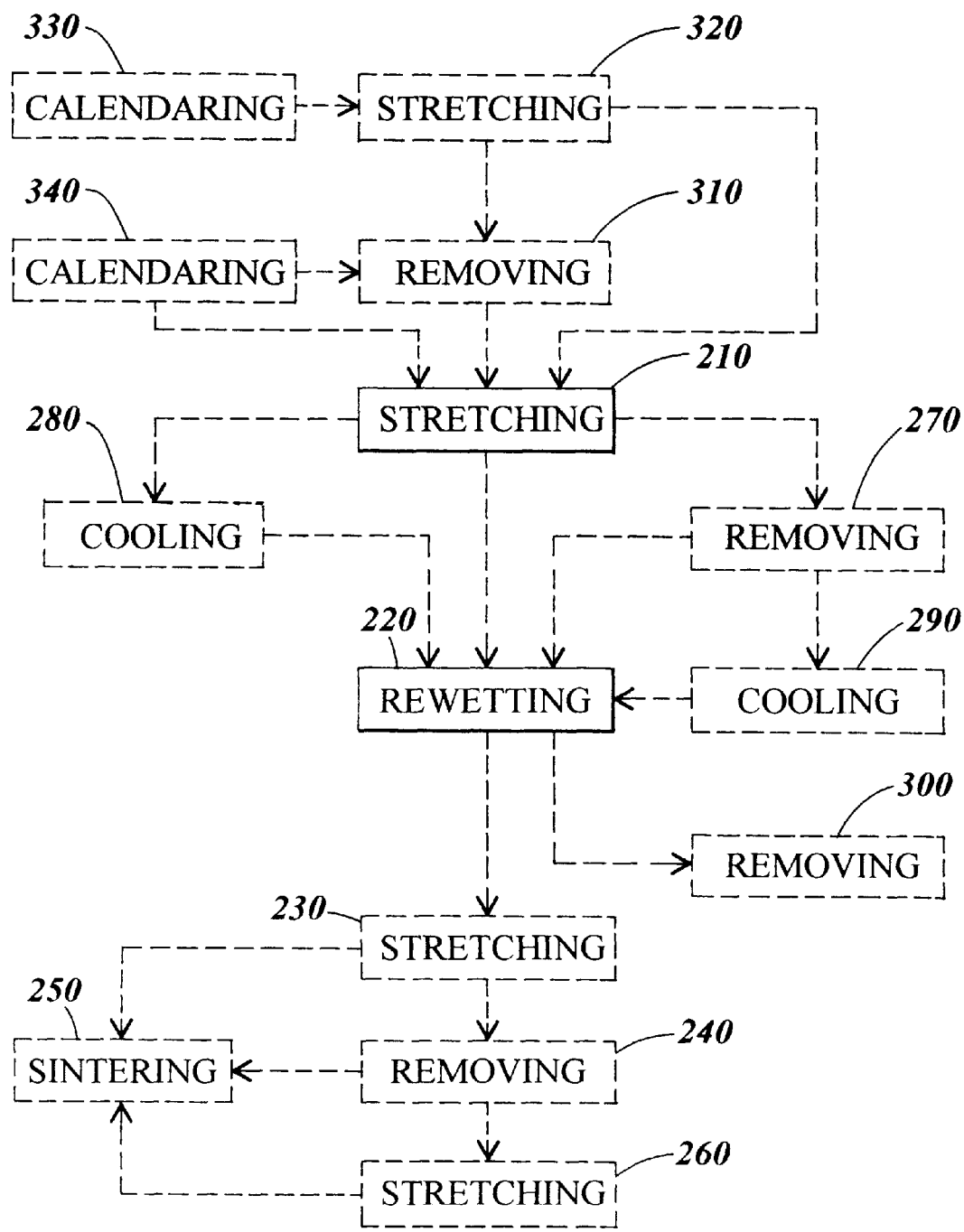
FIG. 2B illustrates exemplary variations of a second embodiment of the invention.

A second, preferred embodiment of the invention is shown in FIG. 2. The second embodiment of the invention differs from the first embodiment, at least in part, by stretching of the expandable polymer before rewetting with a second wettable liquid.

According to an exemplary method of the second embodiment, an expandable polymer is stretched, step 210. Because a second wettable liquid has not been applied, it is preferable that stretching be performed with heat, for example in radiant heat oven set to approximately 705° F., thereby allowing greater stretch ratios. Rewetting, step 220, is then performed by applying a second wettable liquid to the expandable polymer. As discussed in relation to rewetting step 110 of the first embodiment, a wettable liquid may be applied to the expandable polymer in a variety of ways.

Stretching, step 230, is performed as discussed in relation to the stretching step 120 of the first embodiment. Variations, including for example, heating and direction of stretching, discussed in relation to stretching step 120 of the first embodiment are also applicable to stretching step 230 of the second embodiment.

One variation of the second embodiment of the invention involves increased tension on a take-up roller during processing. This will provide a variation in properties of the resulting expandable polymer. Increased tension of the take-up roller will impart some longitudinal orientation to the nodes of the expandable polymer and create a thicker, less dense product than is typical without increased tension on the take-up roller.

Another variation of the second embodiment involves substituting the step of stretching 230 with the application of pressure sufficient to change the structure of the expandable polymer. By way of example, pressure may be applied by the use of rollers to crush the expandable polymer.

The second embodiment of the invention may also include removal of the second wettable liquid from the expandable polymer. Removal of the second wettable liquid, step 240, is optionally performed after the stretching step 230. Further optional variations include single or multi-directional stretching as discussed above in relation to the stretching step 120 of the first embodiment, or sintering, step 250, after removal of the second wettable liquid, step 240.

Alternatively, a third stretching step 260 may be performed after removal of the second wettable liquid, step 240.

A further variation of the second embodiment involves sintering, step 250, after the second stretching step 230, or the removal of the second wettable liquid, step 240, or stretching step 260.

Another variation of the second embodiment includes removal of the first wettable liquid, step 270, after the stretching step 210. According to another variation, cooling, step 280, may be performed prior to the rewetting step 220. Cooling, step 290, may also be performed after optional removal of the first wettable liquid, step 270.

A further variation of the second embodiment includes removal of the second wettable liquid, step 300, after the rewetting step 220. In this variation, the second stretching step 230 is not conducted.

The second embodiment may also include the application of heat during the first stretching step 210. The step of stretching without heat or use of a wettable liquid typically cannot involve high stretch ratios without risk of tearing the expandable polymer.

Further variations of the second embodiment include removal of the first wettable liquid, step 310, prior to the first stretching step 210. Another variation includes preliminary stretching of the expandable polymer, step 320, before the first stretching step 210. Preliminary stretching, step 320, before the first stretching step 210 may be conducted prior to optional removal of the first wettable liquid, step 310, but the invention is not so limited and stretching may be conducted without removal of the first wettable liquid.

A further variation of the second embodiment includes calendaring. As discussed in relation to the first embodiment, calendaring is typically performed during the creation of a flat sheet. The step of calendaring 330, 340 may be conducted shortly after extrusion of the expandable polymer, such as before the step of preliminary stretching 310, the step of removal of the first wettable liquid 310, or stretching step 210.

The embodiments and their variations described above are intended to be representative of the scope of the invention and not limiting. It is also intended to be within the scope of the invention for variations of the embodiments to be applicable to other embodiments. For example, variations of the second embodiment may be used in combination with methods of the first embodiment.

The invention will now be described with respect to various examples involving various forms, beginning with sheets and films.

EXAMPLE #1

Example 1 of the invention, Material D, involves flat material that is stretched in the machine direction according to the second embodiment of the invention. This example provides increased density of the material and an altered node structure from those available by conventional methods.

PTFE resin (Fluon CD-123 obtained from ICI Americas) was blended with ISOPAR-H odorless lubricant solvent (produced by EXXON Corporation) at a level of 19.5% by weight to form a lubricated powder. The lubricated powder was then compressed into a cylinder and ram extruded into a flat sheet 6 inches across and 0.040 inches thick. The flat sheet was then compressed through two heated rolls to form a film having a thickness of 5 mil. The lubricant was then removed from the film by passing the film through a radiant heat oven set to 490° F. to drive off the ISOPAR-H.

Figure 3:
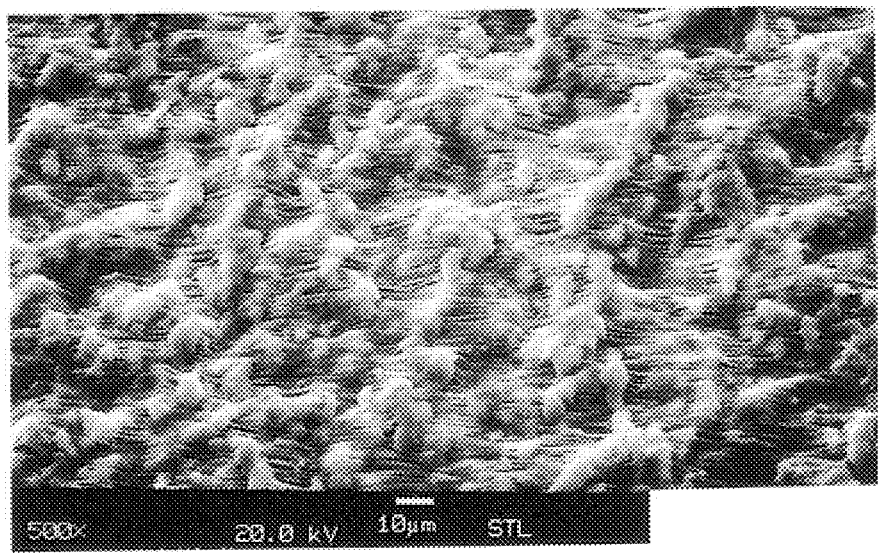
FIG. 3 provides a scanning electron micrograph (SEM) of Material A.

The film was then stretched in the machine direction at a ratio of 10:1 in a radiant oven set at 705° F. to form a Material A. A scanning electron micrograph (SEM) of Material A is shown in FIG. 3. A control experiment was performed where Material A was restretched in the machine direction at a ratio of 1.8:1 with the use of heat but with no wettable liquid to form a Material B shown in FIG. 4. A further experiment was performed to stretch Material A to a ratio of 1.8:1 in the machine direction without the use of heat or wettable liquid to attempt to form a Material C. However, the sample broke before reaching the ratio of 1.8:1. Materials A and B represent samples prepared according to conventional methods. The attempt to form Material C demonstrates the need for heat in conventional stretching methods.

Figure 5:
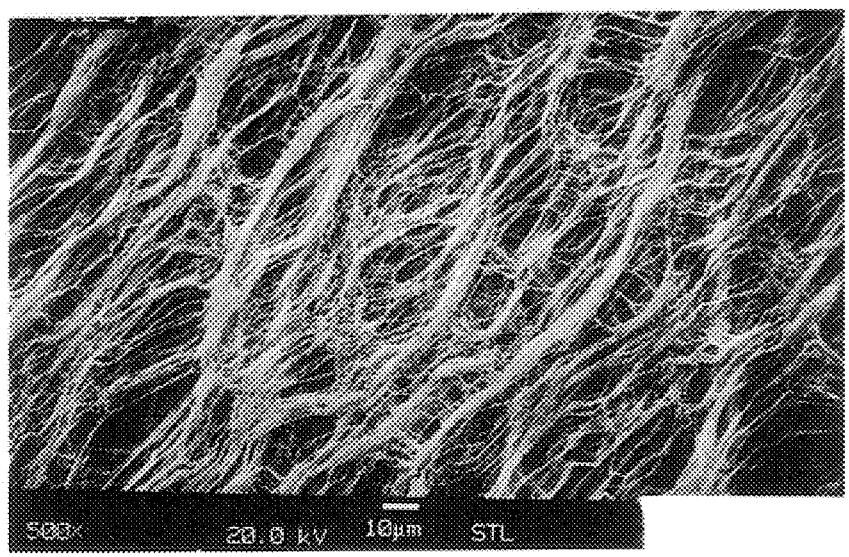
FIG. 5 provides an SEM of Material D of the invention.

According to Example 1 of the invention, Material A is rewet with the ISOPAR-H wettable liquid and stretched in the machine direction at a ratio of 1.8:1 at room temperature to form a Material D. FIG. 5 shows the elongated nodes and alignment of the fibrils of Material D.

As summarized in Table 1, the film produced by Example 1, Material D, is thinner and has a higher density than a similarly-stretched film produced by a conventional method, Material B. The node structure that is obtained by these two methods differs drastically, as shown in FIGS. 4 and 5.

Figure 4:
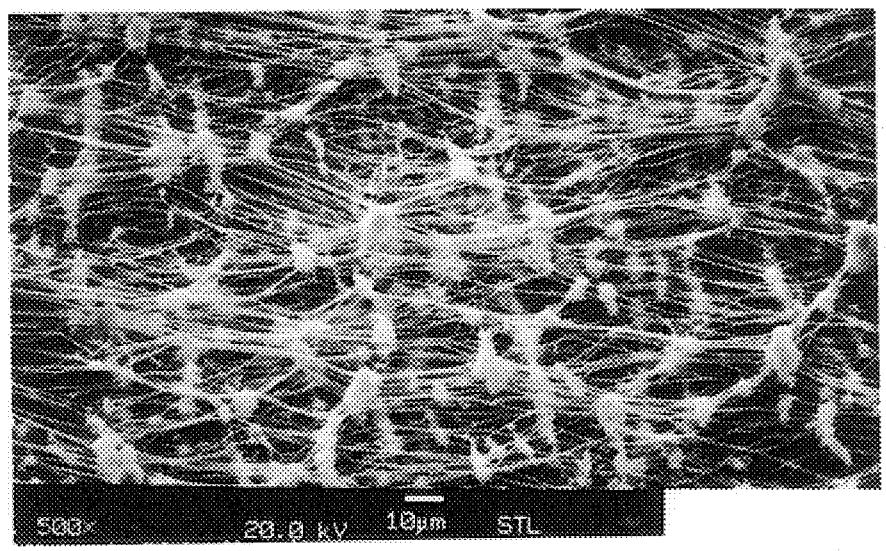
FIG. 4 provides an SEM of Material B.

FIGS. 4 and 5 illustrate that by stretching the material wet, a substantially different node structure is obtained than when conventional methods are used. Material B, shown in FIG. 4, is formed conventionally without wettable liquid and with heat and has a structure where the nodes are connected by fibrils that have a substantial amount of open space between them. Material D, shown in FIG. 5, the film formed by the method of Example 1 involving wettable liquid and no heat, consists of densely packed fibrils and drawn out nodes. As shown in Table 1, a lower thickness and a higher density are obtainable by using the method of Example 1.

TABLE 1

| Mat'l. | First MD Ratio | Wet/ Dry | Hot/ Cold | Second MD Ratio | Thickness Mil | Density (g/cm³) | Machine Direction LTS (lbf) | LTS (psi) | Elong (in) | Elong (%) | Transverse Direction LTS (lbf) | LTS (psi) | Elong (in) | Elong (%) |
|---|---|---|---|---|---|---|---|---|---|---|---|---|---|---|
| A | 10:1 | Dry |  | 1:1 | 1.8 | 0.629 | 11.98 | 6656 | 0.75 | 50 | 0.05 | 27.8 | 23 | 1533 |
| B | 10:1 | Dry | Hot | 1.83:1 | 1.7 | 0.416 | 6.55 | 3853 | 0.4 | 26.6 | 0.03 | 15.7 | 22 | 1467 |
| C | 10:1 | Dry | Cold | 1.83:1 | Broke |  |  |  |  |  |  |  |  |  |
| D | 10:1 | Wet | Cold | 1.83:1 | 1.3 | 0.954 | 3.25 | 2503 | 0.25 | 25 | 0.04 | 26.9 | 26 | 2600 |

EXAMPLE #2

Example 2 of the invention involves a flat material that is stretched in the transverse direction according to the second embodiment of the invention to provide a thin, dense uniform material that has a low porosity. The same lubricated powder of Example 1 is compressed into a cylinder and ram extruded into a flat sheet 6 inches across and 0.040 inches thick. The flat sheet is then compressed through two heated rolls to form a film having a thickness of 10 mil, twice the thickness of the film of Example 1. The ISOPAR-H is then driven off by passing the film through a radiant oven set to 490° F. The film is then stretched in the machine direction, in a radiant oven set at 705° F. at a ratio of 6:1 to form a Material E.

Two control experiments were performed at the same transverse stretch ratio. A first control sample, Material F, was created with heat and no wettable liquid; the other sample, Material G, was created at room temperature also with no wettable liquid.

Figure 6:
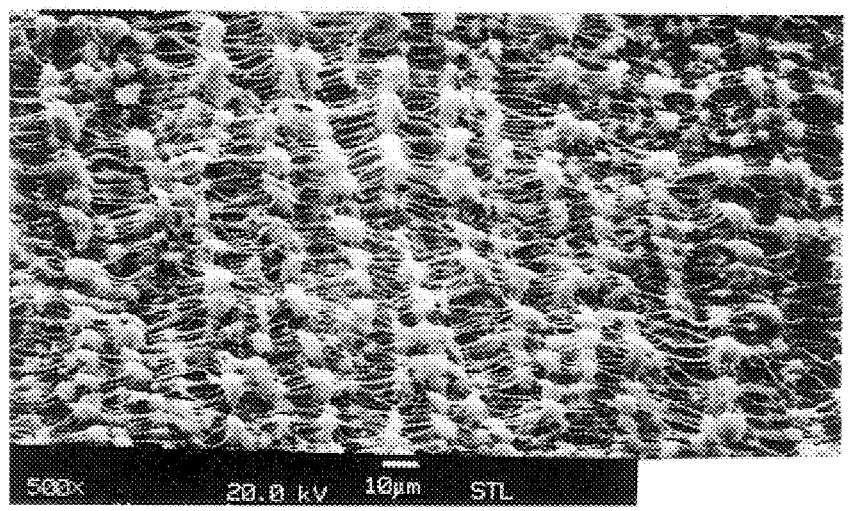
FIG. 6 provides an SEM of Material F.

Material F was made by stretching Material E in the transverse direction, with heat to a 12:1 stretch ratio. Material F has a star-like structure. FIG. 6 shows a scanning electron micrograph (SEM) of Material F. Material F has a very inconsistent thickness that ranged from 4.3 mil in the center to 1 mil at the edges. The average density of this material is 0.319 g/cm³.

Figure 7:
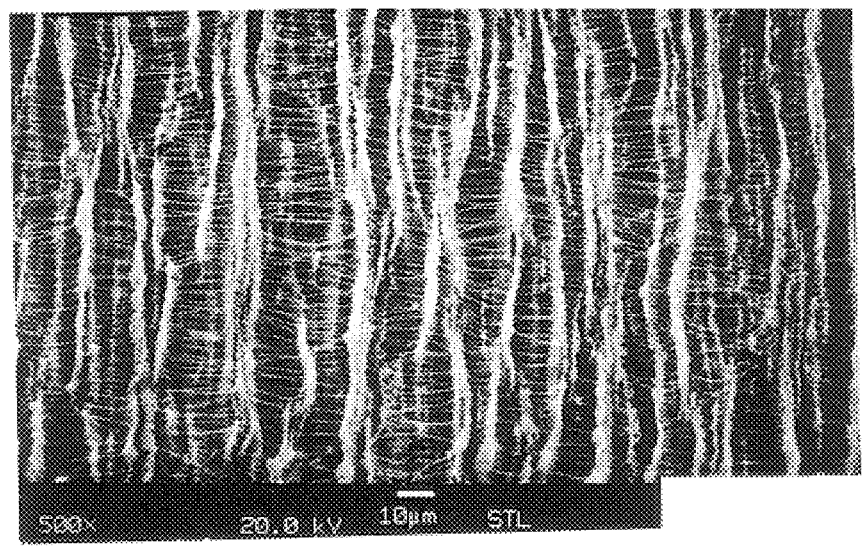
FIG. 7 provides an SEM of Material G.

Material G, another control sample, was made like Material F, except that stretching to a 12:1 ratio was performed at room temperature. A scanning electron micrograph (SEM) of Material G, is shown in FIG. 7. Material G has long ordered nodes with an internodal distance of about 15–30 microns. The density of Material G is 0.348 g/cm³, similar to the other control, Material F.

Figure 8:
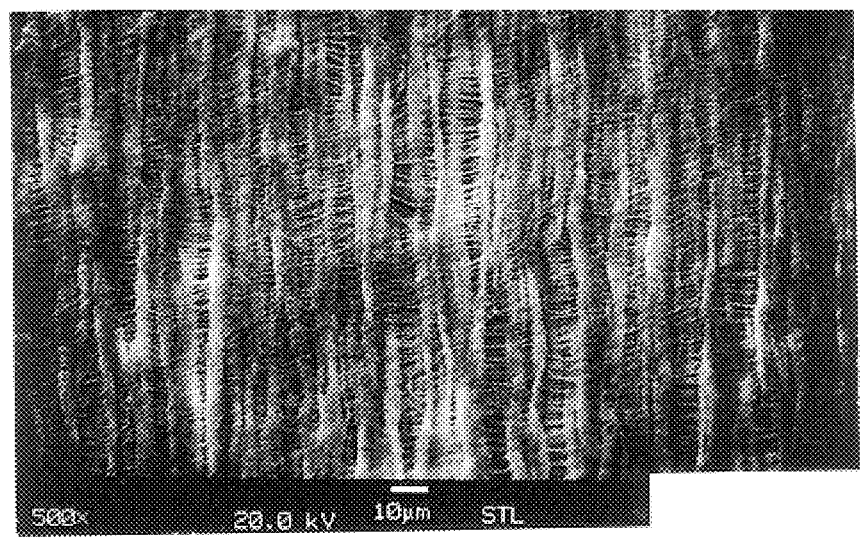
FIG. 8 provides an SEM of Material H of the invention.

According to one variation of the invention, Material E is wet with the ISOPAR-H wettable liquid and stretched in the transverse direction at a ratio of 12:1 at room temperature to form a Material H. FIG. 8 is a scanning electron micrograph of Material H. Material H has a node structure that has long drawn out nodes and very small internodal distances between and including 0 to 10 microns. The thickness of material H is consistently 0.5 mils, and the density of Material H is 1.228 g/cm³, which is approximately four times higher than control materials, Materials F and G.

Figure 9:
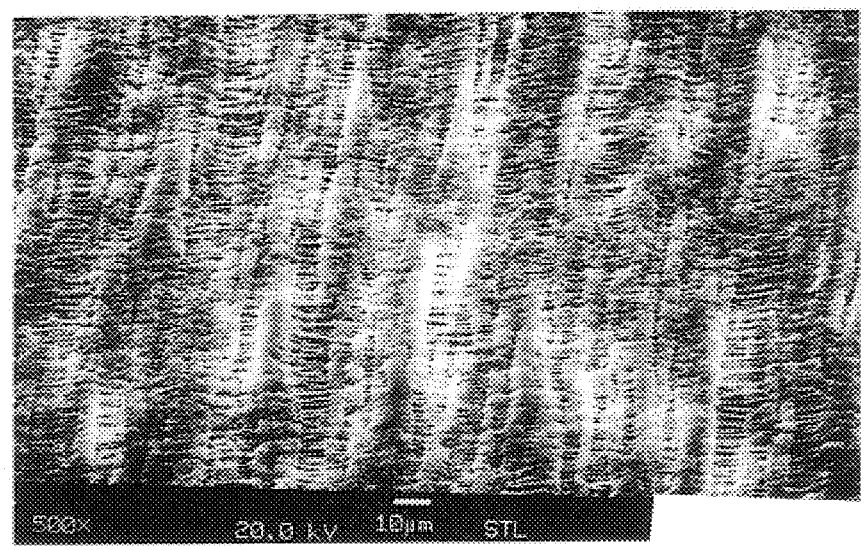
FIG. 9 provides an SEM of Material I of the invention.

Material I, shown in FIG. 9, is material that started out as material H. The wettable liquid was then removed and the material was stretched a second time. This second stretch was in the transverse direction with heat at a ratio of 2:1.

Figure 10:
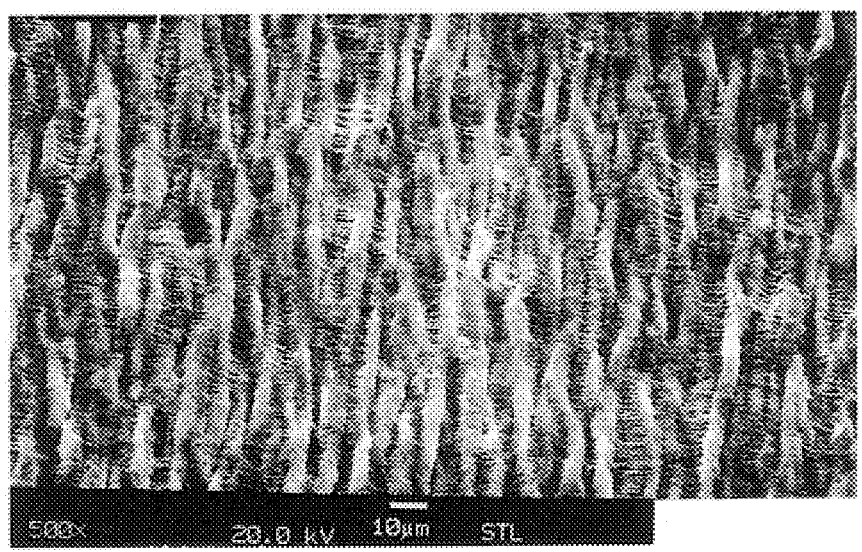
FIG. 10 provides an SEM of Material J of the invention.

Another variation of the invention, Material J, involves increasing tension on the take-up roller to stretch the material in the machine direction during stretching in the transverse direction. Material J is very similar to Material H involving wetting Material E with wettable liquid prior to transverse stretching at room temperature. Increased tension on the take up roller imparts some longitudinal orientation to the nodes. Material J was slightly thicker than Material H, 0.63 mils vs. 0.5 mils, and slightly less dense, 1.158 g/cm³ vs. 1.228 g/cm³. As shown in FIG. 10, Material J has long wavy nodes and was very consistent across the material.

Materials H and J were stretched with the wettable liquid and were much more consistent in thickness and node structure than the two control samples, Materials F and G. The node structure and internodal distance of the materials were also drastically different. Materials H and J, processed by the inventive method, had a density four times higher and were significantly thinner with a different overall feel, than Materials F and G that were processed conventionally.

TABLE 2

| Mat'l | MD Ratio | TD Ratio | Hot/ Cold | Wet/ Dry | Thickness Mil | Density (g/cm³) | Machine Direction LTS (lbf) | LTS (psi) | Elong (in) | Elong (%) | Transverse Direction LTS (lbf) | LTS (psi) | Elong (in) | Elong (%) |
|---|---|---|---|---|---|---|---|---|---|---|---|---|---|---|
| F | 6:1 | 12:1 | Hot | Dry | 4.30 | 0.319 | 2.6 | 605 | 0.7 | 49 | 0.26 | 60.4 | 13 | 867 |
| G | 6:1 | 12:1 | Cold | Dry | 1.87 | 0.348 | 1.93 | 1032 | 1.3 | 89 | 0.34 | 182 | 6.5 | 433 |
| H | 6:1 | 12:1 | Cold | Wet | 0.50 | 1.228 | 2.86 | 5720 | 1.5 | 100 | 0.35 | 431 | 4.25 | 425 |
| I | 6:1 | 1) 12:1; 2) 2:1 | 1) Cold; 2) Hot | 1) Wet; 2) Dry | 1.10 | 0.877 | 2.52 | 4582 | 0.8 | 53 | — | — | — | — |
| J | 6:1 | 12:1 + MD tension | Cold | Wet | 0.63 | 1.158 | 3.62 | 5746 | 1.3 | 87 | 0.43 | 683 | 5.7 | 380 |

EXAMPLE #3

Example 3 of the invention involves a flat material that is stretched in the transverse direction according to the second embodiment of the.invention to provide a thin, dense uniform material that has a low porosity. The same lubricated powder of Example 1 is compressed into a cylinder and ram extruded into a flat sheet 6 inches across and 0.040 inches thick. The flat sheet is then compressed through two heated rolls to form a film having a thickness of 5 mil. A first wettable liquid was then removed by passing the film through an oven. The film was then stretched in the machine direction at an elevated temperature to a ratio of 6:1. The control sample, labeled as Dry in Table 3, was then stretched in the transverse direction to the given ratio. This transverse stretching was done at room temperature at a line speed of 5 feet per minute. A sample according to the invention, labeled Wet in Table 3, was first soaked in a second wettable liquid and then stretched to the same transverse stretch ratios as the control sample.

TABLE 3

| Ratio | Thickness (Inches) | | Density (g/cm³) | |
|---|---|---|---|---|
| | Wet | Dry | Wet | Dry |
| 2:1 | .0030 | .0040 | 1.742 | 0.348 |
| 3:1 | .0028 | .0035 | 1.767 | 0.339 |
| 4:1 | .0025 | .0030 | 1.189 | 0.298 |
| 5:1 | .0020 | .0028 | 0.828 | 0.393 |
| 6:1 | .0015 | .0025 | 0.997 | 0.246 |
| 7:1 | .0004 | .0035 | 0.920 | 0.390 |
| 8:1 | .0005 | .0020 | 1.028 | 0.336 |
| 9:1 | .0003 | .0015 | 1.644 | 0.288 |

The thickness of the sample according to the invention was less than the control sample at every stretch ratio. The density of the inventive sample was found to be much higher than the control. The sample according to the invention was consistent at all ratios tested and it did not rip. The control material was not consistent and it had a tendency to rip. The overall look and feel of the materials was drastically different. The dry processed material had a tendency to shrink and had noticeable striations in it.

The present invention is applicable to a wide variety of product configurations. The following examples illustrate various embodiments of the invention involving tubes.

EXAMPLE #4

Example 4 involves longitudinal stretching of a tube according to the first embodiment of the invention. PTFE resin, Fluon CD-123, was blended with ISOPAR-H odorless solvent at a level of 17% by weight. The lubricated powder was then compressed into a cylinder and ram extruded into a 6 mm-diameter tube. The tube was then soaked in wettable liquid, ISOPAR-H, and stretched longitudinally at room temperature. The tube could easily be stretched to a ratio of 3:1. However, an attempt to stretch the 6 mm-diameter tube at room temperature to a ratio of 3:1 without wettable liquid resulted in the tube breaking.

EXAMPLE #5

Example 5 involves stretching of tubes both radially and longitudinally according to the second embodiment of the invention. A benefit of this example is a very thin, high density tube with a small internodal distance. As in Example 4, PTFE resin, Fluon CD-123, is blended with ISOPAR-H odorless solvent at a level of 17% by weight. The lubricated powder is then compressed into a cylinder and ram extruded into a 2 mm-diameter tube. The ISOPAR-H is driven off in a convection oven at 250° F. The tube is then expanded longitudinally at a rate of 5 inches/sec in a convection oven at a temperature of 320° C.

Figure 11:
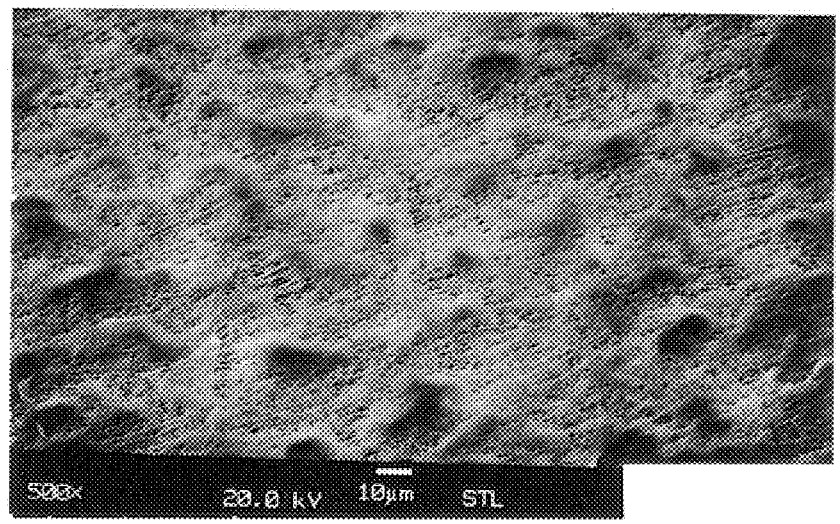
FIG. 11 provides an SEM of Material K of the invention.

The tube is then rewet with ISOPAR-H and stretched over a 19 mm mandrel. The ISOPAR-H is driven off in a convection oven at 250° F. The tube is then sintered in a convection oven at 360° C. The resulting tube, Material K shown in FIG. 11, has a thickness of 0.5 mil and has an inner porosity of <1 $\mu$m. The density of Material K is approximately 1.25 g/cm³.

Radial expansion over the 19 mm mandrel is not possible without the addition of the wettable liquid. An attempt to put a non-sintered tube over the same mandrel when it was not wet with wettable liquid resulted in a longitudinal split of the tube.

EXAMPLE #6

This example involves changing the node structure and density of an ePTFE tube by stretching it longitudinally while it was wet with wettable liquid. As in Example 4, PTFE resin, Fluon CD-123, is blended with ISOPAR-H odorless solvent at a level of 17% by weight. The lubricated powder is then compressed into a cylinder and ram extruded into a 6 mm-diameter tube.

Figure 12:
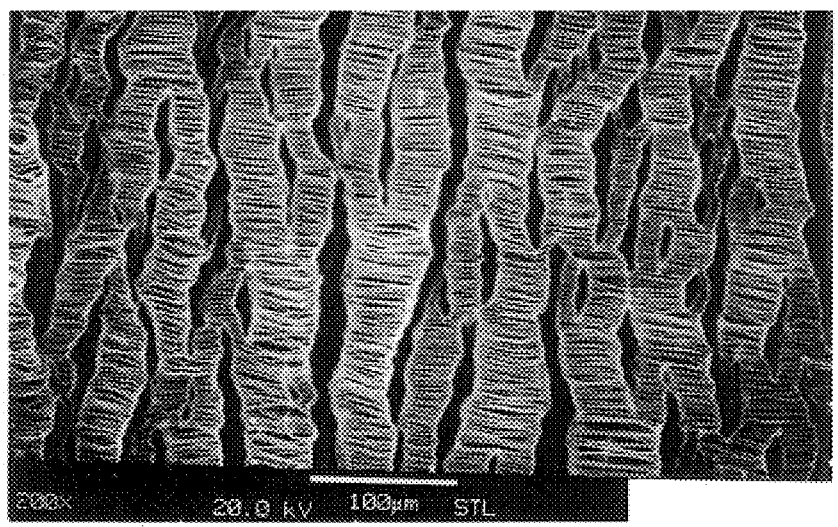
FIG. 12 provides an SEM of Material L.
Figure 13:
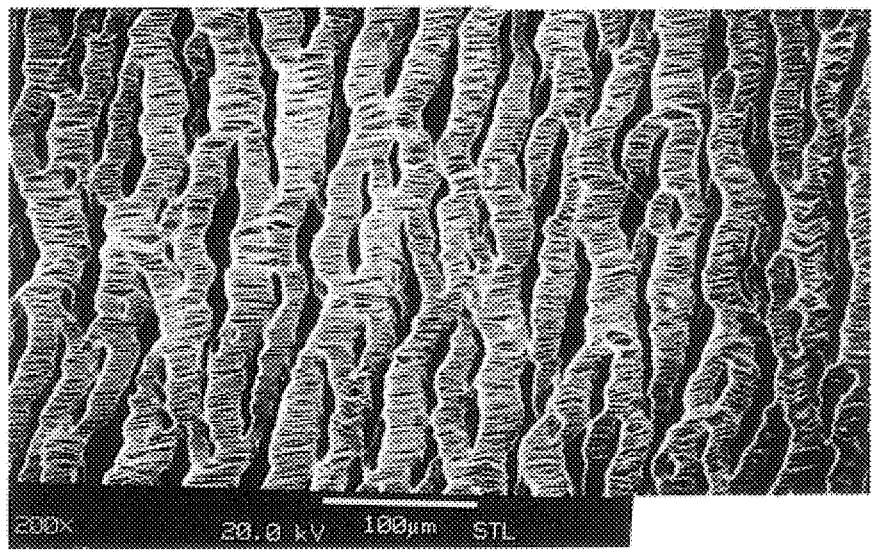
FIG. 13 provides an SEM of Material M.

Two control samples were prepared according to conventional methods using the above extrudate. Material L, shown in FIG. 12, was formed by stretching from 15"–45" with heat and then sintering. Material M, shown in FIG. 13, was formed by stretching from 15" to 30" with heat and then stretching from 30"–45" at room temperature, without the use of wettable liquid, followed by sintering.

Figure 14:
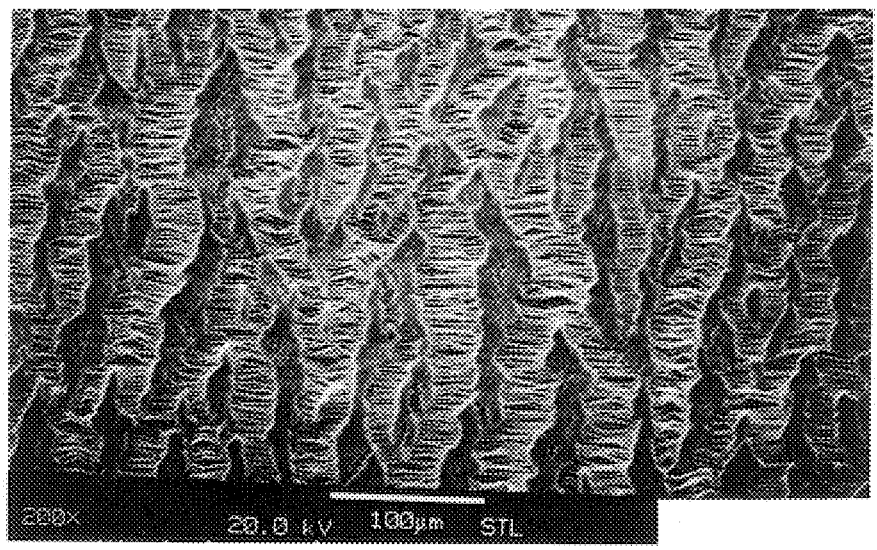
FIG. 14 provides an SEM of Material N of the invention.
Figure 15:
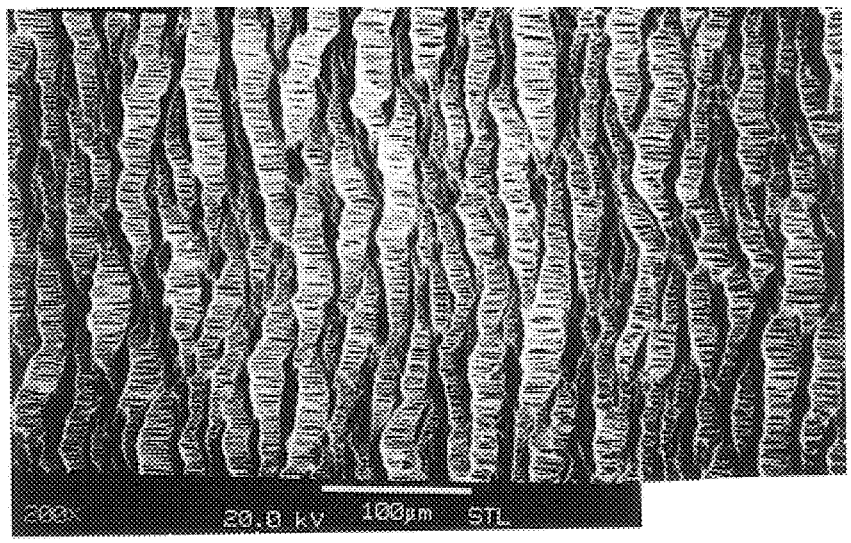
FIG. 15 provides an SEM of Material O of the invention.

Material N, shown in FIG. 14, was formed in accordance with the second embodiment of the invention by first stretching from 15"–30" with heat. It was then wet with the wettable liquid and stretched from: 30"–45" at room temperature. The wettable liquid was then removed and sintering was performed to create Material N. Material O, shown in FIG. 15, was created in accordance with the first embodiment of the invention by wetting with a wettable liquid, then stretching from 15"–20" at room temperature. The wettable liquid was then removed and stretching with heat longitudinally to 45" was performed, followed by sintering.

Material N has a lower internodal distance than the conventional sample Material L. When compared to Material N, Material M was found to have approximately the same internodal distance but with smaller nodes. Material O has a very tight internodal distance and very small nodes when compared to the conventional sample, Material L. All three samples have a higher water entry pressure than the control with Material O being the highest. The only other mechanical property that was changed was suture retention strength, see Table 4.

TABLE 4

| Mat'l | LTS (lbf) | RTS (lbf) | SRT (lbf) | WEP (psi) | ID (in) | Wall Thickness (in) | Density g/cm³ |
|---|---|---|---|---|---|---|---|
| L | 48.36 | 17 | 0.27 | 227 | 0.234 | 0.014 | 0.712 |
| M | 46.06 | 17 | 0.23 | 312 | 0.234 | 0.015 | 0.634 |
| N | 42.70 | 17 | 0.19 | 300 | 0.236 | 0.016 | 0.596 |
| O | 46.46 | 20 | 0.22 | >365 | 0.220 | 0.013 | 0.912 |

EXAMPLE #7

A further example of the invention involves a tube comprised of layers with varying porosity. Variation in porosity can allow enhanced blood flow through a vascular graft, while still enabling tissue to grow into the external surface of the graft. It can also provide for selective filtration through the various pore size layers. Vascular grafts prepared in a layered fashion consist of a highly stretched inner layer mounted on a 6 mm mandrel that is wrapped with a tight porosity ePTFE film and covered with a high porosity outer layer. The resulting tube has a smooth, silky feel with a 10 mil wall thickness. By use of the second embodiment of the present invention, the node structure of one or more of the layers of the tube can be altered.

Figure 16:
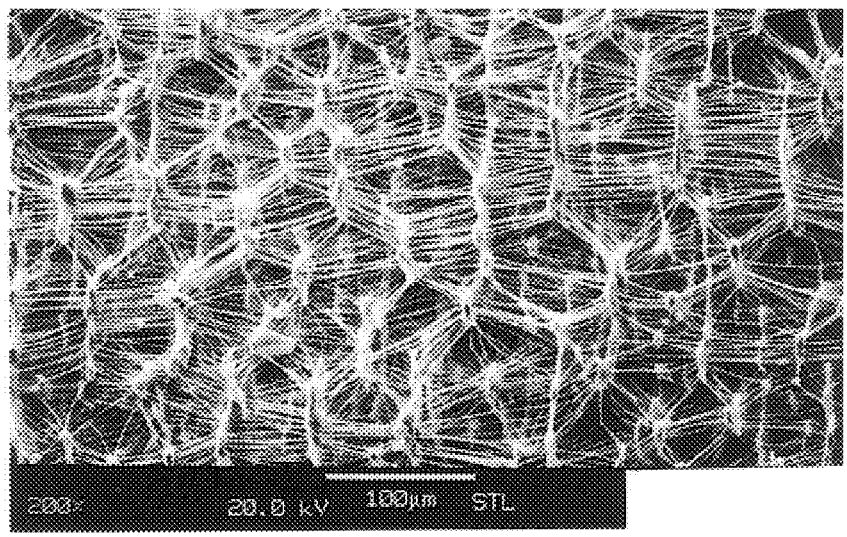
FIG. 16 provides an SEM of an exterior of Sample P.
Figure 17:
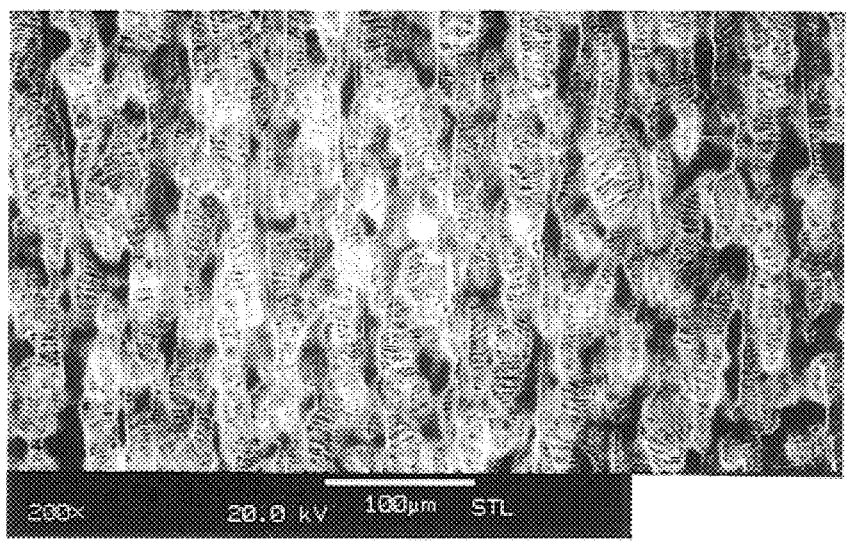
FIG. 17 provides an SEM of an interior of Sample P.
Figure 18:
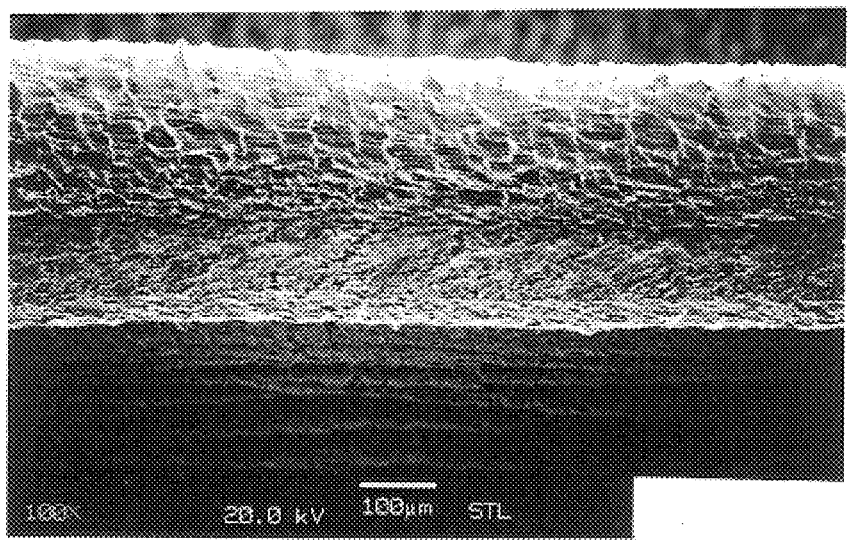
FIG. 18 provides an SEM of a cross-section of Sample P.

Sample P, shown in FIGS. 16–18, is an example of a vascular graft prepared according to steps described in U.S. Pat. No. 5,824,050, incorporated by reference herein. A highly stretched and sintered graft is placed onto a mandrel where it is wrapped, covered with a sintered cover and sintered together. FIG. 16 illustrates the structure of an exterior surface, and FIG. 17 illustrates an interior surface. FIG. 18 provides a cross-sectional view, showing the changing structure along the radius of the graft.

Figure 19:
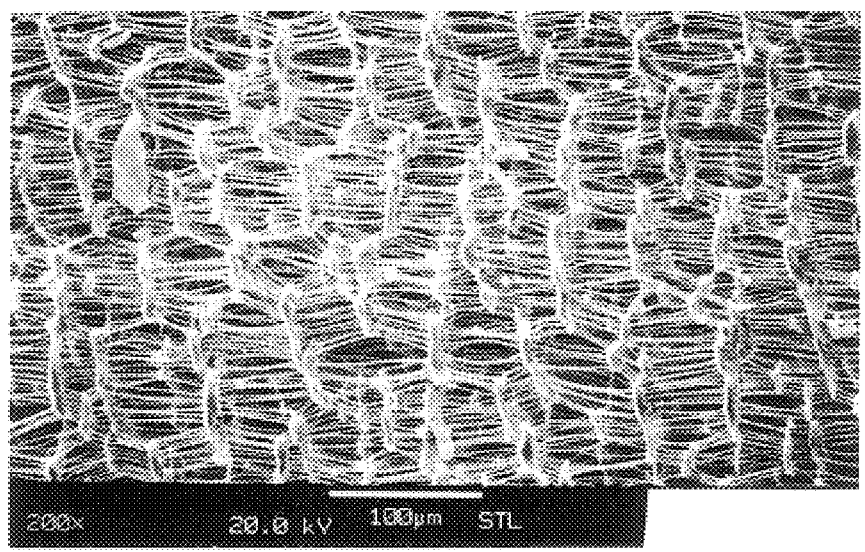
FIG. 19 provides an SEM of an exterior of Sample Q of the invention.

Sample Q is a graft that is made with the same materials as Sample P, but the highly stretched graft inner layer in an unsintered state is rewet with ISOPAR-H, placed on a mandrel where it is then wrapped with tight porosity ePTFE film. The ISOPAR-H is then run off with heat at either 120° C. for 10 minutes or 200° C. for 3 minutes. A sintered cover is prepared by stretching a second tube over a 10 mm mandrel. The expanded tube is then placed over the wrapped inner layer. The entire assembly is then sintered together. Rewetting results in the inner layer having a reduced porosity when compared to Sample P, see FIGS. 19–21. FIG. 19 shows an exterior of Sample Q, while FIGS. 20 and 21 are interior and cross-sectional views of Sample Q, respectively.

Figure 22:
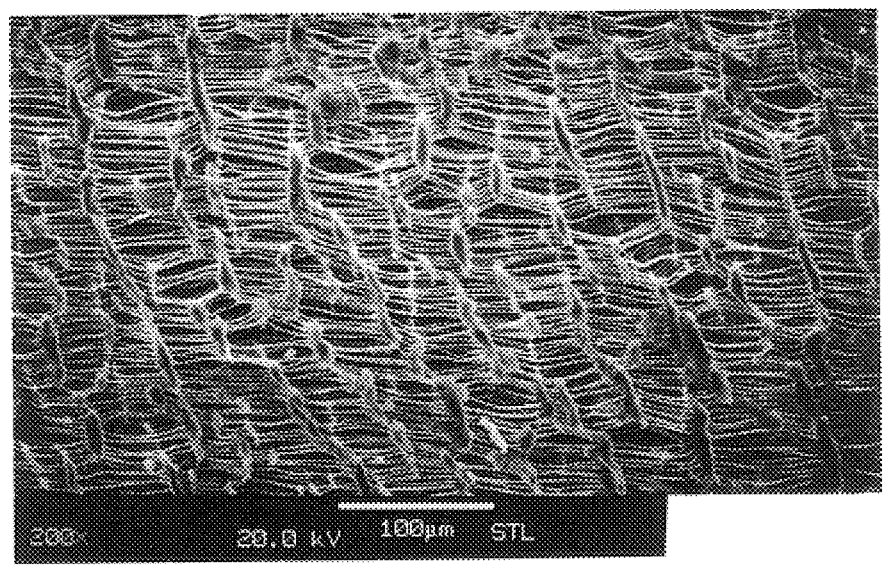
FIG. 22 provides an SEM of an exterior of Sample R of the invention.

Sample R is a graft that is constructed like Sample Q, except that the wrapped inner layer is covered with a non-sintered cover that is wet with ISOPAR-H. The ISOPAR-H is then run off with heat and the entire assembly is then sintered together. See FIGS. 22–24 for views of an exterior, interior and cross-section of Sample R, respectively.

Figure 25:
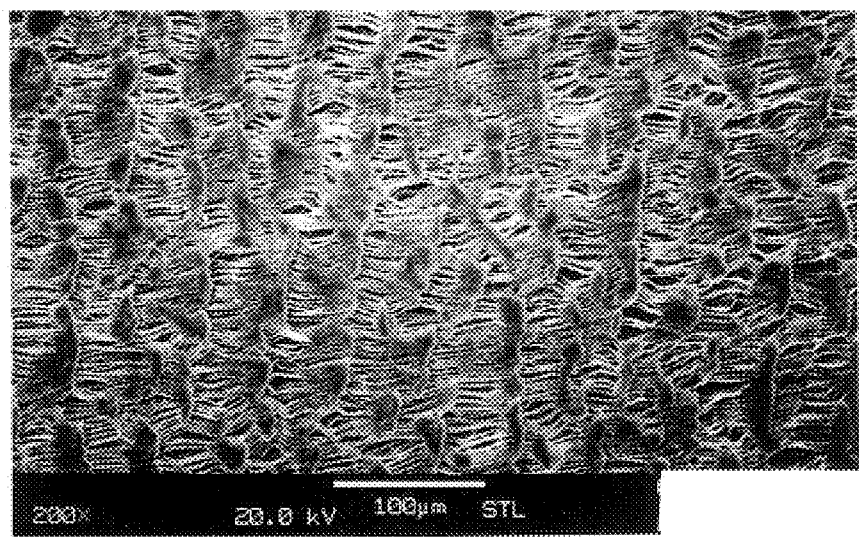
FIG. 25 provides an SEM of an exterior of Sample S of the invention.
Figure 26:
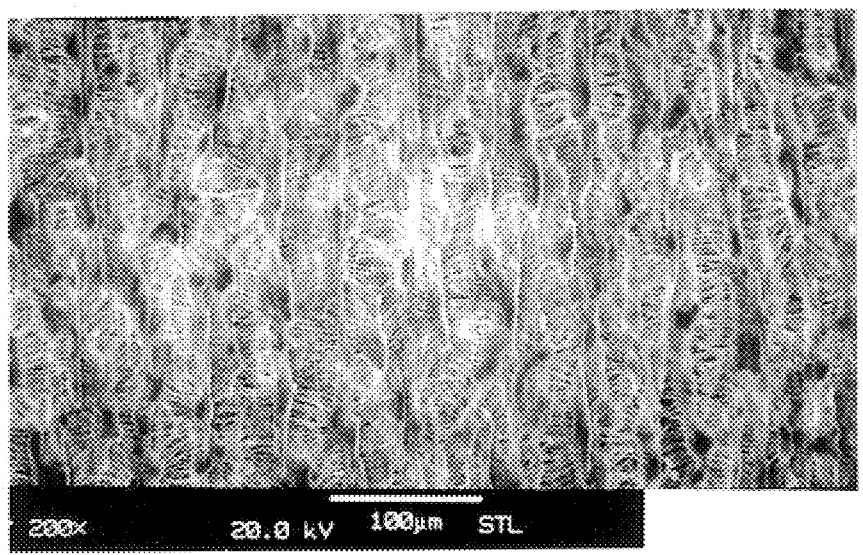
FIG. 26 provides an SEM of an interior of Sample S of the invention.
Figure 27:
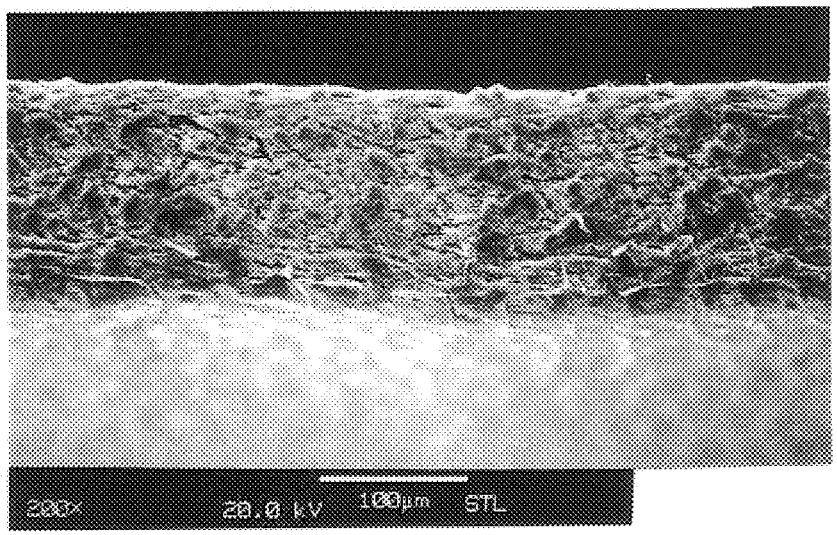
FIG. 27 provides an SEM of a cross-section of Sample S of the invention.

Sample S is a graft that is made with a sintered inner layer that is radially stretched by placement on a mandrel, wrapped and then covered with a non-sintered cover that is wet with ISOPAR-H. The ISOPAR-H is then run off with heat and the entire assembly is then sintered together. See FIGS. 25–27 for an exterior, interior and cross-section of Sample S, respectively.

Figure 20:
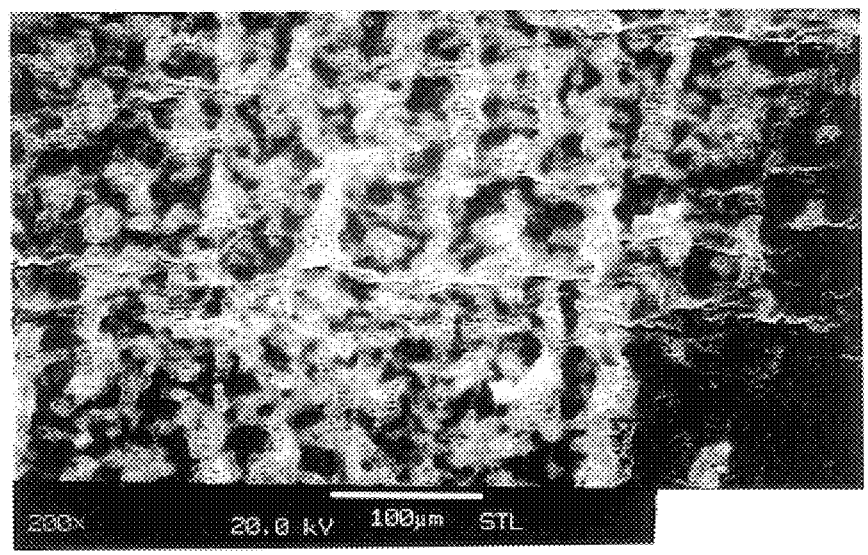
FIG. 20 provides an SEM of an interior of Sample Q of the invention.
Figure 21:
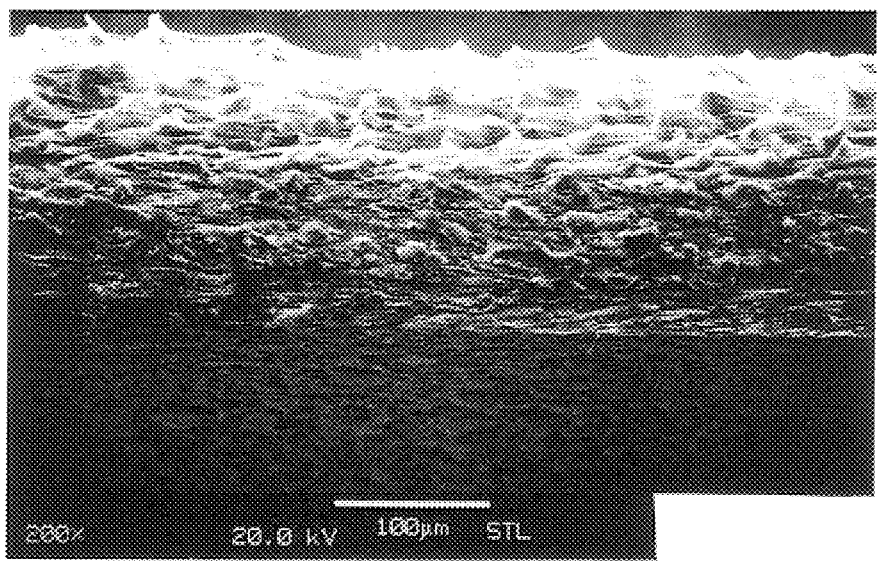
FIG. 21 provides an SEM of a cross-section of Sample Q of the invention.
Figure 23:
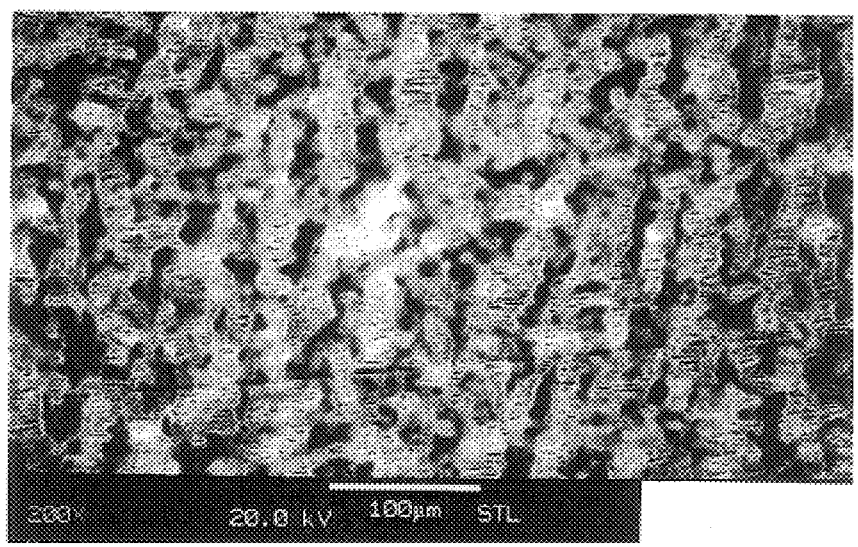
FIG. 23 provides an SEM of an interior of Sample R of the invention.
Figure 24:
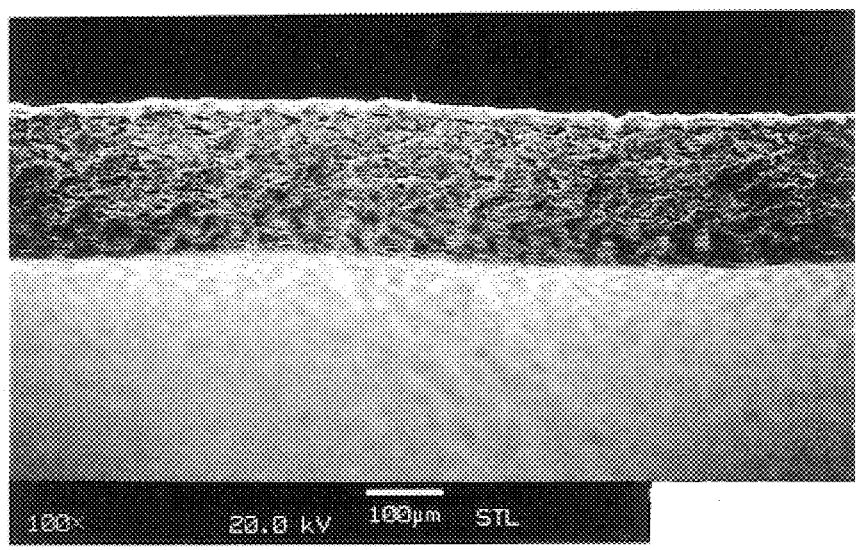
FIG. 24 provides an SEM of a cross-section of Sample R of the invention.

With reference to FIGS. 17, 20 and 23, the samples that were made with the non-sintered method for the inner layer, Samples Q (FIG. 20) and R (FIG. 23) have a very tight inner porosity when compared to the method disclosed in U.S. Pat. No. 5,824,050 (FIG. 17). Samples R and S, made with the wet stretch method for the cover, have higher tear strength values than samples using a sintered cover, Samples P and Q.

Another embodiment of the invention involves the use of a crusher, such as a roller, to crush the inner layer after radial stretching and before application of the ePTFE film, thereby reducing the porosity of the inner layer. Samples T—W illustrate the change in properties from the use of the crusher. Except for crushing, Samples T—W are otherwise, processed like Samples P—S, respectively. See Table 5 for comparison.

TABLE 5

| Sample | Inner | Wrap | Outer | Other | LTS (lbf) | RTS (lbf) | SRT (lbf) | Tear (lbf) | Where |
|---|---|---|---|---|---|---|---|---|---|
| P | Sintered | (7.5:1) | Sintered | | 31.7 | 164 | 1.4 | 0.16 | cover |
| Q | Non-Sintered | (7.5:1) | Sintered | | 32.1 | 115 | 0.99 | 0.09 | cover |
| R | Non-Sintered | (7.5:1) | Non-sintered | | 34.1 | 142 | 1.34 | 0.26 | cover |
| S | Sintered | (7.5:1) | Non-sintered | | 33.6 | 153 | 2.1 | 0.26 | cover |
| T | Sintered | (7.5:1) | Sintered | Crusher | 32.8 | 155 | 1.42 | 0.07 | cover |
| U | Non-Sintered | (7.5:1) | Sintered | Crusher | 32.8 | 153 | 1.24 | 0.08 | cover |
| V | Non-Sintered | (7.5:1) | Non-sintered | Crusher | 34.0 | 133 | 0.81 | 0.24 | cover |
| W | Sintered | (7.5:1) | Non-sintered | Crusher | 33.1 | 167 | 2.17 | 0.19 | cover |

The present invention is applicable to a wide variety of product configurations. The following example illustrates an embodiment of the invention involving the application of pressure.

EXAMPLE #8

Figure 28:
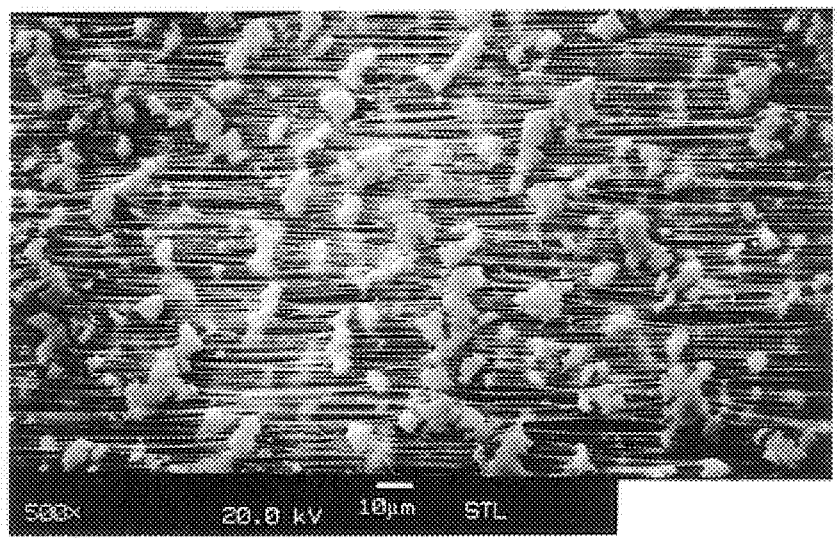
FIG. 28 provides an SEM of Material X.
Figure 29:
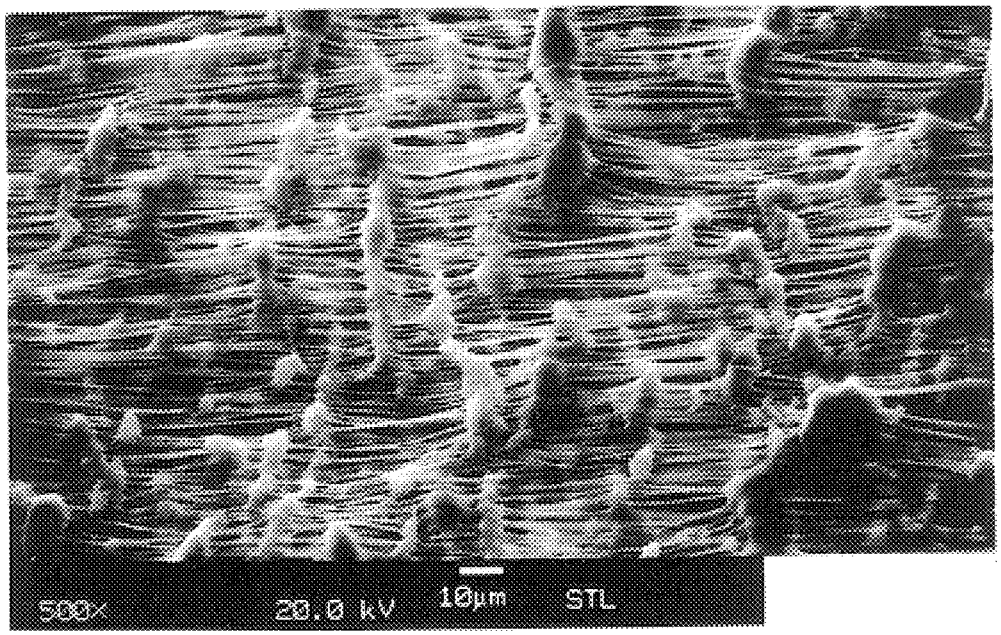
FIG. 29 provides an SEM of Material Y of the invention.

Example 8 of the invention involves a flat material that has pressure applied to it according to the second embodiment of the invention to provide a thin, dense uniform material that has a low porosity. The same lubricated powder of Example 1 is compressed into a cylinder and ram extruded into a flat sheet 6 inches across and 0.040 inches thick. The flat sheet is then compressed through two heated rolls to form a film having a thickness of 5 mil. A first wettable liquid was then removed by passing the film through an oven. The film was then stretched in the machine direction at-an elevated temperature to a ratio of 7.5:1 to form Material X, shown in FIG. 28. A roll of Material X was then wet with the ISOPAR-H wettable liquid. Pressure was then applied to the roll of wet material using a set of rollers to form Material Y, Shown in FIG. 29. Material Y has a much higher fibril density than Material X and has a denser overall look to it. Material Y was thinner than Material X, 1.2 mil and 3.1 mil respectively. The density of Material Y was 0.776 g/cm$^3$ compared to Material X which had a density of 0.375 g/cm$^3$.

In addition to the embodiments and examples discussed above, wettable liquid may be applied during initial wetting or rewetting by the use of increased or decreased temperature and/or pressure. Increased or decreased temperature and/or pressure can reduce processing time and enhance the saturation of the expandable polymer.

The techniques of the present invention may be employed to create implantable prosthetic devices that are adapted for delivery of bioactive materials. For example, vascular grafts with multiple lumens may be created using the techniques described herein. The physical structure components in such prosthetic devices is discussed in further in detail U.S. Pat. No. 5,411,550, entitled "Implantable Prosthetic Device for the Delivery of a Bioactive Material," the contents of which are incorporated herein by reference.

Expandable polymers of the present invention have wide ranging applications, such as devices for in vivo implantation, prostheses intended for placement or implantation to supplement or replace a segment of a natural biological blood vessel, and supports for tissue repair, reinforcement or augmentation. Specific products include but are not limited to heart valves, sutures, vascular access devices, vascular grafts, shunts and catheters. Other products include single and multilayered membranes. Multilayered membranes containing regions of selective porosity and chemistry are useful in the medical diagnostic: and the filtration industries. For example, some clinical diagnostic test strips contain multilayer membranes with selective binding sites in each layer to capture analytes from blood, serum, and the like, when the test liquid is flowing through it.

According to additional aspects of the invention, expandable polymers may be formed into sheets, grafts, electrical insulation and other known polymer applications. These applications include among other devices, vascular grafts, endovascular liners and grafts, prosthetic patches, vascular access devices, shunts, catheters, sutures or implantable tissue augmentation devices, such as those used in cosmetic surgery. According to yet a further feature, the articles of manufacture include single and multilayered membranes formed from sheets. Such membranes may be employed in clinical diagnostic test strips or in filtration devices.

The invention can be applied to other processes where stretching or expanding of material is involved. It will thus be seen that the invention efficiently attains the objects set forth above, including providing implantable devices having tailored porosity and/or chemistry characteristics. Since certain changes may be made in the above constructions and the described methods without departing from the scope of the invention, it is intended that all matter contained in the above description or shown in the accompanying drawings be interpreted as illustrative and not in a limiting sense. By way of example, any known methods for varying the porosity and/or chemistry characteristics of implantable prostheses, such as varying the lubrication level in the blended pasted, viewed in combination with the disclosed methods are considered to be within the scope of the present invention. Additionally, any methods for combining resins, pastes, billets or extrudates, according to the methods of the invention, are also considered to be within the scope of the present invention.

Having described the invention, what is claimed as new and protected by Letters Patent is:

1. A method for forming an article, comprising the steps of:
   mixing an expandable fluoropolymer resin with a first wettable liquid to form a mixture;
   extruding said mixture to form an extruded article; and
   rewetting said extruded article with a second wettable liquid to form a wetted material.

2. The method of claim 1, wherein said step of rewetting occurs at a temperature below the boiling temperature of said second wettable liquid.

3. The method of claim 1, wherein said first and second wettable liquids are the same composition.

4. The method of claim 1, wherein said article is in the shape of a tube.

5. The method of claim 1, wherein said article is in the shape of a flat sheet.

6. A method for forming an article, comprising the steps of:
   mixing an expandable polymer resin with a first wettable liquid to form a mixture;
   extruding said mixture to form an extruded article;
   rewetting said extruded article with a second wettable liquid to form a wetted material;
   stretching said wetted material.

7. The method of claim 6, further comprising the step of stretching said extrude article, after said step of extruding.

8. The method of claim 7, further comprising the step of removal of said first wettable liquid before said step of stretching said extruded article.

9. The method of claim 8, further comprising after said step of stretching said wetted material, the step of sintering.

10. The method of claim 8, further comprising the step of removing said second wettable liquid from said wetted material to form a dried material.

11. The method of claim 10, further comprising the step of stretching said dried material, after said step of removing said second wettable liquid.

12. The method of claim 11, further comprising, the step of sintering, after said final step of stretching said dried material.

13. The method of claim 8, wherein said step of stretching said wetted material is performed at a temperature less than 80° F.

14. The method of claim 6, wherein said step of stretching said wetted material is performed at a temperature less than 80° F.

15. The method of claim 6, further comprising, after said step of stretching said wetted material, the steps of:
   removing said second wettable liquid from said wetted material to form a dried material;
   stretching said dried material; and
   sintering.

16. The method of claim 6, wherein said expandable polymer is a fluoropolymer.

17. The method of claim 6, wherein said expandable polymer is a polyolefin.

18. The method of claim 6, wherein said article is in the shape of a tube.

19. The method of claim 6, wherein said article is in the shape of a flat sheet.

20. The method of claim 6, wherein said expandable polymer is a fluoropolymer.

21. A method for forming an article, comprising the steps of:
   mixing an expandable polymer resin with a first wettable liquid to form a mixture;
   extruding said mixture to form an extruded article;
   rewetting said extruded article with a second wettable liquid to form a wetted material;
   stretching said extruded article, after said step of extruding;
   removal of said first wettable liquid before said step of stretching said extruded article; and
   stretching said wetted material, after said step of wetting;
   wherein said wetted material is in the shape of a tube and said step of stretching consist of stretching in a radial direction to increase a diameter of said wetted material.

22. The method of claim 21, further comprising, after said step of stretching said wetted material, the step of sintering.

23. A method for forming an article, comprising the steps of:
   mixing an expandable polymer resin with a first wettable liquid to form a mixture;
   extruding said mixture to form an extruded article;
   stretching said extruded article, after said step of extruding;

removal of said first wettable liquid before said step of stretching said extruded article;

rewetting said extruded article with a second wettable liquid to form a wetted material;

stretching said wetted material, after said step of wetting; and calendaring said extruded material, after said step of extruding.

24. The method of claim 23, further comprising, after said step of stretching said wetted material, the steps of:

removing said second wettable liquid from said wetted material to form a dried material;

stretching said dried material; and sintering.

25. The method of claim 23, wherein said step of stretching said wetted material involves stretching in a machine direction.

26. The method of claim 25, further comprising, after said step of stretching said wetted material, the step of sintering.

27. The method of claim 23, wherein said step of stretching said wetted material involves stretching in a direction transverse to a machine direction.

28. The method of claim 27, further comprising, after said step of stretching said wetted material, the step of sintering.

29. A method for forming an article, comprising the steps of:

mixing an expandable polymer resin with a first wettable liquid to form a mixture;

extruding said mixture to form an extruded article;

rewetting said extruded article with a second wettable liquid to form a wetted material;

stretching said extruded material, after said step of extruding; and removal of said first wettable liquid before said step of stretching said extruded article;

applying pressure, after said step of rewetting.

30. The method of claim 29, further comprising, the step of sintering, after said step of applying pressure.

31. The method of claim 29, wherein a structure of said wetted material is changed by the application of pressure.

32. The method of claim 29, wherein a density of said wetted material is changed by the application of pressure.

33. A method of forming an article from an expandable polymer, comprising the steps of:

rewetting said expandable polymer with a wettable liquid to form a wetted material;

stretching said wetted material.

34. A method for forming an article, comprising the steps of:

mixing an expandable polymer resin with a first wettable liquid to form a mixture;

extruding said mixture to form an extruded article;

calendaring said extruded article;

removal of said first wettable liquid from said extruded article to form a first dried material;

stretching said first dried material;

rewetting said first dried material with a second wettable liquid to form a wetted material;

applying pressure to said wetted material;

removal of said second wettable liquid to form a second dried material;

stretching said second dried material; and sintering.

35. A method for forming an article, comprising:

mixing an expandable polymer resin with a first wettable liquid to form a mixture;

extruding said mixture to form an extruded article;

removal of said first wettable liquid from said extruded article after said extruding;

stretching said extruded article after said removal of said first wettable liquid;

rewetting said extrudable article with a second wettable liquid to form a wetted material after said stretching of said extruded article; and stretching said wetted material.

36. A method for forming an article, comprising the step of:

mixing an expandable polymer resin witha first wetttable liquid to form a mixture;

ram extruding siad mixture to an extruded article; and rewetting said extruded article with a second wettable liquid to form a wetted materil.

* * * * *

UNITED STATES PATENT AND TRADEMARK OFFICE
CERTIFICATE OF CORRECTION

PATENT NO. : 6,616,876 B1
DATED : September 9, 2003
INVENTOR(S) : Roger Labrecque et al.

It is certified that error appears in the above-identified patent and that said Letters Patent is hereby corrected as shown below:

<u>Title page,</u>
Item [*] Notice, should read :
-- [*]   Notice:  Subject to any disclaimer, the term of this patent is extended or adjusted under 35 U.S.C. 154(b) by 312 days. --

Signed and Sealed this

Twenty-seventh Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,616,876 B1
DATED : September 9, 2003
INVENTOR(S) : Lebrecque et al.

It is certified that error appears in the above-identified patent and that said Letters Patent is hereby corrected as shown below:

<u>Column 4,</u>
Line 29, replace "(intermodal distance)" with -- (internodal distance) --;

<u>Column 11,</u>
Line 27, replace "The.density of the.inventive" with
-- The density of the inventive --;

<u>Column 18,</u>
Line 40, replace "resin witha first" with -- resin with a first --;
Line 42, replace "siad" with -- said --;
Line 44, replace "materil" with -- material --.

Signed and Sealed this

Eighteenth Day of May, 2004

JON W. DUDAS
*Acting Director of the United States Patent and Trademark Office*